(12) United States Patent
Sun

(10) Patent No.: US 8,993,629 B2
(45) Date of Patent: Mar. 31, 2015

(54) VISCOELASTIC SYSTEM FOR DRIFT REDUCTION

(75) Inventor: Jinxia Susan Sun, Hopewell Junction, NY (US)

(73) Assignee: Akzo Nobel N.V., Arnhem (NL)

( * ) Notice: Subject to any disclaimer, the term of this patent is extended or adjusted under 35 U.S.C. 154(b) by 124 days.

(21) Appl. No.: 13/061,806

(22) PCT Filed: Sep. 1, 2009

(86) PCT No.: PCT/EP2009/061232
§ 371 (c)(1),
(2), (4) Date: Mar. 2, 2011

(87) PCT Pub. No.: WO2010/026127
PCT Pub. Date: Mar. 11, 2010

(65) Prior Publication Data
US 2011/0166235 A1    Jul. 7, 2011

Related U.S. Application Data

(60) Provisional application No. 61/094,123, filed on Sep. 4, 2008.

(30) Foreign Application Priority Data

Oct. 9, 2008    (EP) ..................... 08166169

(51) Int. Cl.
| | |
|---|---|
| *A01N 37/10* | (2006.01) |
| *A01N 25/30* | (2006.01) |
| *A01N 37/40* | (2006.01) |
| *A01N 39/04* | (2006.01) |

(52) U.S. Cl.
CPC ............... *A01N 25/30* (2013.01); *A01N 37/40* (2013.01); *A01N 39/04* (2013.01)
USPC ........................................ 514/571

(58) Field of Classification Search
None
See application file for complete search history.

(56) References Cited

U.S. PATENT DOCUMENTS

| | | | |
|---|---|---|---|
| 4,528,023 A | 7/1985 | Ahle | |
| 5,118,444 A | 6/1992 | Nguyen | |
| 5,459,210 A | 10/1995 | Kihara et al. | |
| 2005/0130842 A1* | 6/2005 | Fleute-Schlachter et al. | ............... 504/206 |

(Continued)

FOREIGN PATENT DOCUMENTS

| | | |
|---|---|---|
| EP | 0 290 416 A2 | 11/1988 |
| EP | 1 366 662 A1 | 12/2003 |
| GB | 2 267 825 A | 12/1993 |

(Continued)

OTHER PUBLICATIONS

European Search Report Application No. 08166169.6; Completion date Mar. 5, 2009.

(Continued)

*Primary Examiner* — Ernst V Arnold
*Assistant Examiner* — Jianfeng Song
(74) *Attorney, Agent, or Firm* — Matthew D. Kellam

(57) ABSTRACT

The invention relates to a viscoelastic system for drift reduction for pesticidal formulations, and the use thereof, wherein said formulation comprising at least one nitrogen-based cationic surfactant and at least one pesticide, wherein said pesticide contains at least one acid functional group associating with said cationic surfactant thereby forming a viscoelastic formulation.

2 Claims, 2 Drawing Sheets

The effect of tallowalkyl trimethyl ammonium chlorides . (1%) on the viscosity of different concentration of 2,4-D DMA solution

(56) References Cited

U.S. PATENT DOCUMENTS

2006/0025321 A1* 2/2006 Treybig et al. ............... 510/382
2006/0194699 A1* 8/2006 Moucharafieh et al. ...... 504/206

FOREIGN PATENT DOCUMENTS

| WO | WO 95/16352 | | 6/1995 | |
| WO | WO 96/32839 | | 10/1996 | |
| WO | WO 00/15037 | | 3/2000 | |
| WO | WO 01/89302 | A2 | 11/2001 | |
| WO | WO-0189302 | * | 11/2001 | |
| WO | WO 0189302 | * | 11/2001 | ............. A01N 25/30 |
| WO | WO 02/12165 | A1 | 2/2002 | |
| WO | WO 02/091829 | A1 | 11/2002 | |
| WO | WO 03/067983 | A1 | 8/2003 | |
| WO | WO 03/068377 | A1 | 8/2003 | |
| WO | WO 03/093641 | A1 | 11/2003 | |
| WO | WO 2005/015996 | A1 | 2/2005 | |
| WO | WO 2006/034459 | A1 | 3/2006 | |
| WO | WO 2007/031438 | A2 | 3/2007 | |
| WO | WO 2007/109791 | A2 | 9/2007 | |
| WO | WO 2008/094588 | A1 | 8/2008 | |

OTHER PUBLICATIONS

International Search Report Application No. PCT/EP2009/061232; Completion date Feb. 10, 2010.

* cited by examiner

Figure 1. The effect of tallowalkyl trimethyl ammonium chlorides . (1%) on the viscosity of different concentration of 2,4-D DMA solution
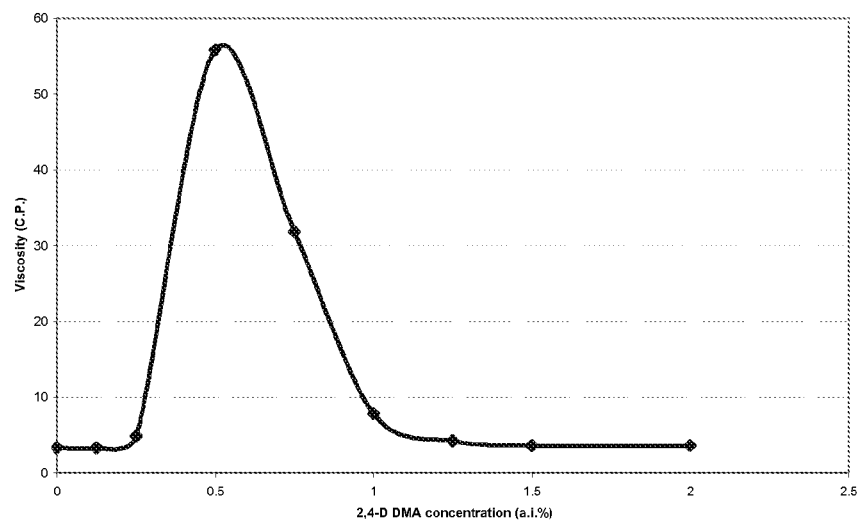

Figure 2. The different drifting effect between 2,4-D DMA treatments
Note : The first row (top row) of water sensitive papers shows 1% (a.i.) 2,4-D DMA with 0.25% (a.i.) tallowalkyl trimethyl ammonium chlorides. The second row (bottom row) of water sensitive papers shows 1% (a.i.) 2,4-D DMA sprayed alone.
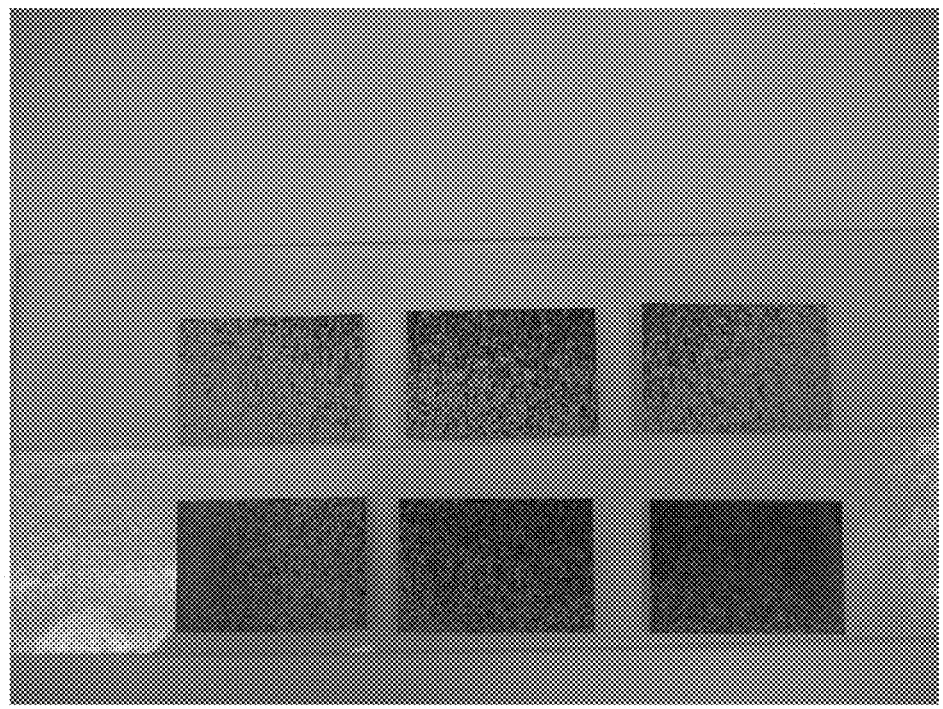

VISCOELASTIC SYSTEM FOR DRIFT REDUCTION

The present case was filed under the Patent Cooperation Treaty on Sep. 1, 2009 and claims priority of European application No. application No. 08166169.6 filed Oct. 9, 2008 and U.S. provisional application No. 61/094,123 filed Sep. 4, 2008.

FIELD OF THE INVENTION

The present invention generally relates to a viscoelastic system for drift reduction whereby the pesticidal active itself acts as the electrolyte to form said viscoelastic system.

BACKGROUND OF THE INVENTION

When pesticide solutions are sprayed by ground spray equipment or aircraft, droplets are produced by the nozzles of the equipment. Many of these droplets can be so small that they stay suspended in air and are carried by air currents until they contact a surface or drop to the ground. A number of factors influence drift, including the physio-chemical properties of the spray mixture, weather conditions, topography, the crop or area being sprayed, application equipment and methods, and decisions by the applicator.

Off-target spray can affect human health and the environment. For example, spray drift can result in pesticide exposures to farm workers, children playing outside, and wildlife and its habitat. Drift can also contaminate a home garden or another farmer's crops, causing illegal pesticide residues and/or plant damage. The proximity of individuals and sensitive sites to the pesticide application, the amounts of pesticide drift, and toxicity of the pesticide are important factors in determining the potential impacts from drift.

The EPA defines pesticide spray drift as the physical movement of a pesticide through air at the time of application or soon thereafter, to any site other than that intended for application (often referred to as off target). EPA does not include in its definition the movement of pesticides to off-target sites caused by erosion, migration, volatility, or contaminated soil particles that are windblown after application, unless specifically addressed on a pesticide product label with respect to drift-control requirements.

Each year there are thousands of reported complaints of off-target spray drift. Reports of exposures of people, plants, and animals to pesticides due to off-target drift (often referred to as "drift incidents") are an important component in the scientific evaluation and regulation of the uses of pesticides. Other routes of pesticide exposure include consuming foods and drinking water which may contain pesticide residues, applying pesticides, and contacting treated surfaces in agricultural, industrial, or residential settings. The EPA considers all of these routes of exposure in regulating the use of pesticides.

In the past, conventional polymers of guar gum, acrylamide and other ethylenically unsaturated monomers have been used as anti-drift agents. It has been generally accepted that polymers which give optimum spray drift control are either non-ionic (eg acrylamide homopolymer) or have relatively low anionic content (e.g. 5 to 30 wt. %) and also have relatively high intrinsic viscosity, for instance above 6 dl/g. Such polymers tend to form viscous aqueous solutions unless used at low concentration. Normal practice is to mix the polymer powder or reverse phase emulsion form with water directly into the spray tank so as to form an aqueous solution of polymer. However, emulsion polymers can be difficult to activate in this situation and polymer powders take a long time to dissolve leading to many large, undissolved particles, resulting in a formulation exhibiting a high viscosity even at a very low polymer concentration. It is therefore sometimes necessary to use more polymer as a result of inefficient dissolution of the polymer in solution, typically on the order of at least 0.05 wt. %. Polymers of intrinsic viscosity in the range 6 to 15 dl/g are also typically utilized in the final spray solution. In addition to the above-problems, such aqueous liquid systems are not shear stable and irreversibly lose their utility due to the fact that high molecular weight polymers undergo mechanical degradation of their molecular weight.

Accordingly, there is a need to reduce the amount of drift exhibited by aqueous liquids which are used in agro applications using non-polymeric drift control agents.

SUMMARY OF THE INVENTION

The present invention generally relates to a viscoelastic system for drift reduction whereby the pesticidal active itself acts as the electrolyte to form said viscoelastic system. The invention of the composition comprises
1) At least one nitrogen based cationic surfactant and
2) A pesticide, especially containing an acid functional group, e.g., compounds that contain at least one carboxylic, sulfonic, citric or phosphonic acid group (except glyphosate) in the form of the free acid or a salt or ester, wherein said pesticide acts as an electrolyte having a moiety that is capable of associating with said cationic surfactant thereby forming a viscoelastic solution.

DETAILED DESCRIPTION OF THE INVENTION

The present invention generally relates to a composition and method for imparting shear stable anti-drifting properties to aqueous pesticidal formulations through the use of one or more viscoelastic surfactants. More specifically, the present invention relates to compositions comprising at least one nitrogen based cationic surfactant in combination with a salt of a pesticide having a moiety that is capable of associating with said cationic surfactant thereby forming a viscoelastic (VES) system. This VES "drift control" system comprising said pesticide can conveniently be applied using conventional spray equipment.

In order to form the VES drift control system of the invention, the pesticides utilized preferably contain an acid functional group, e.g., they contain at least one carboxylic, sulfonic, citric or phosphonic acid group (except glyphosate) which is in the form of the free acid or a salt or ester thereof. These acid functional groups act as electrolytes in the composition to form a viscoelastic system when the composition is diluted to the final use rate. This reduces the amount of resulting satellite drop formation and the drift that causes phytotoxicy on non-targeted species and health hazards and other potential environmental issues.

The composition of the invention can be formulated either in-can or mixed at the tankside. With in-can formulations, there is no viscosity increase in the formulation until it is diluted to the final use rate with water.

On one embodiment, the composition of the invention comprises
1) At least drift control agent which comprises at least one nitrogen based cationic surfactant, and
2) A pesticide containing an acid functional group, e.g., compounds that contain at least one carboxylic, sulfonic, citric or phosphonic acid group (except glyphosate) in the form of the free acid or a salt or ester thereof, wherein said pesticide acts as an electrolyte having a moiety that is capable of associating with the surfactant to form a viscoelastic solution.

The cationic surfactant(s) of said drift control agent self-assemble into long, flexible wormlike micelles alone or in the presence of salt, and the entanglement of these micelles into a transient network imparts viscoelastic properties to the solution. These micelles can thus function as thickening and rheology control agents in aqueous systems, much like polymer thickeners.

The cationic surfactant is employed in an amount sufficient to reduce the spray drift of the aqueous pesticidal formulations during application. When the pesticide is used at the recommended rate, the pesticide salt itself acts as an electrolyte, which can associate as the counter ion with the surfactant ion to form a viscoelastic system. When said cationic surfactant is formulated with high concentrations of the pesticide salt, the high concentration of the pesticide can solubilize the wormlike micelle structure of the surfactants, resulting in a loss of viscosity. However, when diluted to the final use rate, the surfactant itself or combination of same with pesticide salt acts as the counter ion to form wormlike micelles, resulting in the viscosity of the final spray system being restored. In addition, this system is significantly more shear stable than an aqueous pesticidal formulations containing polymer anti-drift agents.

Examples of pesticides employable in the context of the present invention include, but are not limited to pesticide(s), especially containing an acid functional group, e.g., that contain at least one carboxylic, sulfonic, citric or phosphonic acid group (except glyphosate) which is in the form of the free acid or a salt or ester thereof. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters.

The amount of pesticide employed depends on the type of pesticide employed. More commonly used pesticide compounds that can be used within the compositions of the invention include, but are not limited to phenoxy acetic acids, phenoxy propionic acids, phenoxy butyric, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, sulfonylureas, imidazolinones, cyclohexanediones, aryloxyphenoxypropanoates, dichlobenil, isoxaben, and bipyridylium compounds.

Examples of these compounds and their esters that present these characteristics and which can be effectively utilized in accordance with the present invention are:

(R—COO)$_n$—R' wherein R—COO represents an acetate of one of the following acids: arylalanines such as N-benzoyl-N-(3,4-dichlorophenyl)-DL-alanine(benzoylprop), and N-benzoyl-N-(3-chloro-4-fluorophenyl)-Dalanine(flamprop);

aryloxyphenoxypropionic acids such as
(RS)-2-[4-(3,5-dichloro-2-pyridyloxy)phenoxyl propionic acid (chlorazifop), (R)-2-[4-(4-cyano-2-fluorophenoxy) phenoxy]propionic acid (cyhalofop), (RS)-2-[4-(2,4-dichlorophenoxy)phenoxy]propionic acid (diclofop),
(RS)-2-[4-(6-chloroquinoxalin-2-yloxy)phenoxy]propionic acid (quizalofop),
(R)-2-[4-(6-chloroquinoxalin-2-yloxy)phenoxy]propionic acid (quizalofop -P), and
(RS)-2-[4-(α,α,α-trifluoro-p-tolyloxy)phenoxy]propionic acid(trifop);

benzoic acids such as
3,6-dichloroanisic acid (dicamba), and
3,5,6-trichloroanisic acid (tricamba);
cyclohexene oximes such as
(E)-(RS)-3-[1-(allyloxyimino)butyl]4-hydroxy-6,6-dimethyl-2-oxocyclohex-3-enecarboxylic acid (alloxy-dim);
dicarboximides such as
(Z)-2-chloro-3-[2-chloro-5-(cyclohex-1-ene-1,2-dicarboximido)phenyl]acrylic acid (cinidon), and
[2-chloro-5-(cyclohex-1-ene-1,2-dicarboximido)-4-fluorophenoxy]acetic acid (flumiclorac); imidazolinones such as
2-[4,5-dihydro-4-methyl-4-(1-methylethyl)-5-oxo-1H-imidazol-2-yl]4(or5)-methylbenzoic acid (imazamethabenz),
(RS)2-(4-isopropyl4-methyl5-oxo-2-imidazolin-2-yl)quinoline-3-carboxylic acid (imazaquin), and
(RS)-5-ethyl-2-(4-isopropylmethyl-5-oxo-2-imidazolin-2-yl)nicotinic acid (imazethapyr);
nitrophenyl ethers such as
5-(2-chloro-α,α,α-trifluoro-p-tolyloxy)-2-nitrobenzoic acid (acifluorfen),
5-(2,4-dichlorophenoxy)-2-nitrobenzoic acid (bifenox),
O-[5-(2-chloro-α,α,α-trifluoro-p-tolyloxy)-2- nitrobenzoyl] glycolic acid (fluoroglycofen), and
O-[5-(2-chloro-α,α,α-trifluoro-p-tolyloxy)-2-nitrobenzoyl]-DL-lactic acid(lactofen);
phenoxyacetic acids such as
(2,4-dichlorophenoxy)acetic acid (2,4-D),
4-chlorophenoxyacetic acid (4-CPA), and
(4-chloro-2-methylphenoxy)acetic acid (mcpa);
phenoxybutyric acids such as
4-(2,4-dichlorophenoxy)butyric acid (2,4-DB), and
4-(4-chloro-o-tolyloxy)butyric acid (mcpb);
phenoxypropionic acids such as
(RS)-2-(2,4-dichlorophenoxy)propionic acid (dichlorprop),
(R)-2-(2,4-dichlorophenoxy)propionic acid-(dichlorprop-P),
(R)-2-(4-chloro-o-tolyloxy)propionic acid(mecoprop-P);
picolinic acids such as
3,6-dichloropyridine-2-carboxylic acid (clopyralid),
4amino-3,5-dichloro-6-fluoro-2-pyridyloxyacetic acid (fluroxypyr), and
4-amino-3,5,6-trichloropyridine-2-carboxylic acid (picloram);
pyrazolphenyls such as
5-[4-bromo-1-methyl-5-(trifluoromethyl) pyrazol-3-yl]-2-chloro-4-fluorobenzoic acid (fluazolate), and
2-chloro-5-(4-chloro-5-difluoromethoxy-1-methylpyrazol-3-yl)-4-fluorophenoxyacetic acid (pyraflufen);
pyridazinones such as
2-chloro-5-[1,6-dihydro-5-methyl-6-oxo-4-(trifluoromethyl)pyridazin-1-yl]4-fluorophenoxyacetic acid (flufenpyr),
5-bromo-1,6-dihydro-6-oxo-1-phenylpyridazin-4-yloxamic acid(oxapyrazon), and
(RS)-hexahydro-4-hydroxy-3,6-dioxopyridazin-4-ylacetic acid (pydanon);
pyridines such as
2-difluoromethyl-5-(4,5-dihydro-1,3-thiazo1-2-yl)-4-isobutyl6-trifluoromethylnicotinic acid (thiazopyr), and
3,5,6-trichloro-2-pyridyloxyacetic acid (Triclopyr);
pyrimidinyloxybenzoics such as
2,6-bis(4,6-dimethoxypyrimidin-2-yloxy)benzoic acid (Bispyribac), and
2-(4,6-dimethoxypyrimidin-2-yloxy)-6-(1-methoxyiminoethyl) benzoic acid (Pyriminobac)
2-chloro-6-(4,6-dimethoxypyrimidin-2- ylthio)benzoic acid (pyrithiobac);

quinolinecarboxylics such as
3,7-dichloroquinoline-8-carboxylic acid(Quinclorac), and 7-chloro-3-methylquinoline-8-carboxylic acid (Quinmerac);
sulfonanilides such as
3-chloro-2-(5-ethoxy-7-fluoro[1,2,4]triazolo[1,5-clpyrimidin-2-ylsulfonamido)benzoic acid (Cloransulam);
triazolones such as
(RS)-2-chloro-3-{2-chloro-5-[4-(difluoromethyl)-4,5-dihydro-3-methyl-5-oxo-1H-1,2,4-triazol-1-yl]-4fluorophenyl)propionic acid(Carfentrazone);
unclassified such as
[2-chloro-4-fluoro-5-(5,6,7,8-tetrahydro-3-oxo-1H,3H-[1,3,4]thiadiazolo[3,4-a]pyridazin-1-ylideneamino)phenylthio]acetic acid (Fluthiacet);
uracils such as
1-(allyloxycarbonyl)-1-methylethyl 2-chloro-5-[1,2,3,6-tetrahydro-3-methyl-2,6-dioxo-4-(trifluoromethyl)pyrimidin-1-yl]benzoic acid (Butafenacil), and
2-chloro-5-(1,2,3,6-tetrahydro-3-methyl-2,6-di-oxo-4-trifluoromethylpyrimidin-1-yl)benzoicacid (flupropasil);
Phosphinic acid derivatives such as
4-[hydroxyl(methyl)phosphinoyl]-DL-homoalanine (glufosinate) and the salts thereof;
Sulfonylurea derivatives such as
3-chloro-5-(4,6-dimethoxypyrimidin-2-ylcarbamoylsulfamoyl-1-methylpyrazole carboxylic acid (Halosulfuron) EP-A0282613,
3-[(4,6-dimethoxypyrimidin-2-ylcarbamoyl)sulfamoyll-6-trifluoromethyl)nicotinic acid (Flupyrsulfuron) see Brighton Crop Prot. Conf. Weeds, 1995, p. 49),
2-[[[[(4,6-dimethoxy-2-pyrimidinyl)amino]carbonyl] amino]sulfonyl]-4-[[(methylsulfonyl)amino]methyl]benzoic acid(Mesosulfuron),
3-chloro-5-(4,6-dimethoxypyrimidin-2-ylcarbamoylsulfamoyl)-1-methylpyrazole-4-carboxylicacid (EP-A 0 282 613),
5-(4,6-dimethylpyrimidin-2-yl carbamoylsulfamoyl)-1-(2-pyridyl)pyrazole-4-carboxylic acid (NC-330, see Brighton Crop Prot. Conference 'Weeds' 1991, Vol. 1, p 45et seq.),
2-[4-dimethylamino-6-(2,2,2-trifluoroethoxy)-1,3,5-triazin-2-ylcarbamoylsulfamoyl]-m-toluic acid(Triflusulfuron),
3-(4-ethyl-6-methoxy-1,3,5-triazin-2-yl)-1-(2,3-dihydro-1, 1-dioxo-2-methylbenzo[b]thiophen-7-sulfonyl)urea (EP-A 0 796 83);
and urea derivatives The following classes of cationic surfactants are useful to form a viscoelastic system with pesticide, especially acid functional ones, e.g., compounds that contain at least one carboxylic, sulfonic or phosphonic acid group which is in the form of the free acid or a salt or ester.

A first class of nitrogen-containing surfactants is represented by general formula (A), below.

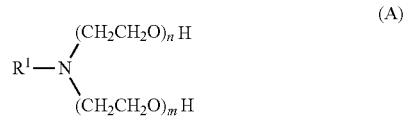

(A)

where $R^1$ is C12 to C30 linear or branched, saturated or unsaturated hydrocarbon chain, in another embodiment, from about 16 to about 22 carbon atoms; n=8 and m=1-8, wherein n and m preferably equal to 1 to 4; in another embodiment n=1-2, and m=1-2. Non-limiting examples of nitrogen containing surfactants of general formula (A) include, but are not limited to tallowamine-2EO, erucicamine-2EO and mixtures thereof.

A second class of nitrogen-containing surfactants is represented by general formula (B), below

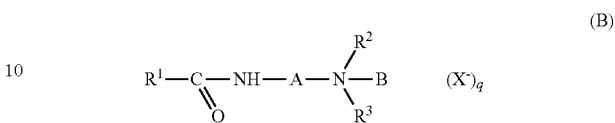

(B)

where $R^1$ is C12 to C30 linear or branched, saturated or unsaturated hydrocarbon chain; in another embodiment having from about 16 to about 22 carbon atoms; A is C1 to C6 linear or branched saturated or unsaturated hydrocarbon chain, and B is $CH_3$, O, or $CH_2$—COO; $X^-$ is a conventional anion, such as $Cl^-$, $Br^-$, $I^-$, $H_2PO_4^-$, $HSO_4^-$, $H_3C$—OSO, $HCO_3^-$ and $H_3C$—$OCO_2^-$. Further anions can be present after an exchange with one or more of the anions mentioned, particularly an exchange with the $HCO_3^-$ and $H_3C$—$OCO_2^-$ anions. For example, the latter anions may also be exchanged to carboxylate anions derived from acids such as acetic acid, propionic acid, 2-ethylhexanoic acid, fatty acids, such as coco fatty acid and tallow fatty acid, salicylic acid, lactic acid, gluconic acid, citric acid, benzoic acid and ethylenediaminetetraacetic acid; and to anions derived from other types of acids, such as methanesulfonic acid, p-toluenesulfonic acid, boric acid and acid clay, q is 0 when B is oxygen or $CH_2$—COO or 1 when B is $CH_3$; $R^2$ and $R^3$ are independently $CH_3$ or $CH_2CH_2OH$. Non-limiting examples of compounds in accordance with formula (B) include tallow dimethylamidopropylamine oxide, erucic dimethylamidopropylamine methyl chloride quaternary, erucic dimethylamido betaine and mixtures thereof.

A third class of nitrogen-containing surfactants is represented by general formula (C), below.

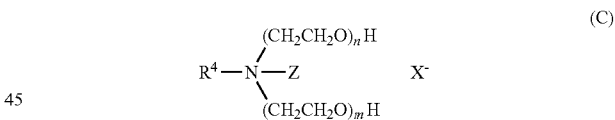

(C)

where $R^4$ is C12 to C30 linear or branched, saturated or unsaturated hydrocarbon chain; in another embodiment having from about 16 to about 22 carbon atoms; n=1-4, m=1-4; in another embodiment n=1-2, and m=1-2, Z is $CH_3$, $C_1$-$C_4$ alkyl or hydroxyl alkyl; and k is a conventional anion, such as $Cl^-$, $Br^-$, $I^-$, $H_2PO_4^-$, $HSO_4^-$, $H_3C$—$OSO_3^-$, $HCO_3^-$ and $H_3C$—$OCO_2^-$. Further anions can be present after an exchange with one or more of the anions mentioned, particularly an exchange with the $HCO_3^-$ and $H_3C$—$OCO_2^-$ anions. For example, the latter anions may also be exchanged to carboxylate anions derived from acids such as acetic acid, propionic acid, 2-ethylhexanoic acid, fatty acids, such as coco fatty acid and tallow fatty acid, salicylic acid, lactic acid, gluconic acid, citric acid, benzoic acid and ethylenediaminetetraacetic acid; and to anions derived from other types of acids, such as methanesulfonic acid, p-toluenesulfonic acid, boric acid and acid clay.

A non-limiting example of a nitrogen containing surfactant according to general structure (C) is erucicamine-2EO methylchloride quaternary.

A fourth class of nitrogen-containing surfactants is represented by general formula (D), below.

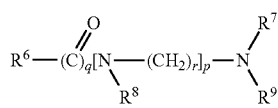

Where $R^6$ is C12 to C30 linear or branched, saturated or unsaturated hydrocarbon chain, in another embodiment having from about 16 to about 22 carbon atoms; q=0 or 1, r=2-6, and p=0-5; $R^7$, $R^8$ and $R^9$ are each independently chosen from H, $CH_3$, $CH_2$—$CH_2$—OH, $CH_2$—COOM or $CH_2CH_2COOM$ (M is comprised of H, Na, K, or NH4) with at least one group being $CH_{2-COOM\,or\,CH_2}CH_2COOM$. Non-limiting examples of nitrogen containing surfactants in accordance with general formula (E) include, but are not limited to coco amphocarboxyglycinate ($R^6$=coco, q=1, r=2, p=1, $R^7$ is $CH_2COO$ Na, $R^8$ is H or $CH_2CH_2OH$, and $R^9$, different than $R^8$, is $CH_2CHOH$ or H), oleylampho polycarboxy glycinate ($R^6$=oleic, q=0, r=3, p=3, and $R^7$, $R^8$ and $R^9$ are $CH_2CH_2COO$ Na), and mixtures thereof.

A fifth class of nitrogen-containing surfactants is represented by general formula (E), below

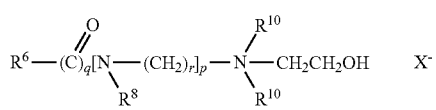

Where $R^6$ is C12 to C30 linear or branched, saturated or unsaturated hydrocarbon chain, in another embodiment having from about 16 to about 22 carbon atoms; q=0 or 1, r=2-6, and p=0-5; $X^-$ is a conventional anion, such as $Cl^-$, $Br^-$, $I^-$, $H_2PO_4^-$, $HSO_4^-$, $H_3C$—$OSO_3^-$, $HCO_3^-$ and $H_3C$—$OCO_2^{31}$. Further anions can be present after an exchange with one or more of the anions mentioned, particularly an exchange with the $HCO_3^{31}$ and $H_3C$—$OCO_2^-$ anions. For example, the latter anions may also be exchanged to carboxylate anions derived from acids such as acetic acid, propionic acid, 2-ethylhexanoic acid, fatty acids, such as coco fatty acid and tallow fatty acid, salicylic acid, lactic acid, gluconic acid, citric acid, benzoic acid and ethylenediaminetetraacetic acid; and to anions derived from other types of acids, such as methanesulfonic acid, p-toluenesulfonic acid, boric acid and acid clay. $R^{10}$ is either $CH_2CH_2OH$ or $CH_3$. Non-limiting examples of the compounds in accordance with formula (F) include tris (2-hydroxyethyl) tallowalkyl ammonium acetate and (2-hydroxyethyl) tallow dimethyl ammonium acetate.

A sixth class of nitrogen-containing surfactants is represented by general formula (F)

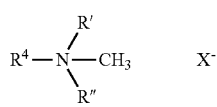

R4 is C12 to C30 to C30 linear or branched, saturated or unsaturated hydrocarbon chain, in another embodiment R4 has from 16 to about 22 carbon atoms;

R' and R" are C1- C4 linear and branched alkyl group, $X^-$ is a conventional anion, such as $Cl^-$, $Br^-$, $I^-$, $H_2PO_4^-$, $HSO_4^-$, $H_3C$—$OSO_3^-$, $HCO_3^-$ and $H_3C$—$OCO_2^-$. Further anions can be present after an exchange with one or more of the anions mentioned, particularly an exchange with the $HCO_3^-$ and $H_3C$—$OCO_2^-$ anions. For example, the latter anions may also be exchanged to carboxylate anions derived from acids such as acetic acid, propionic acid, 2-ethylhexanoic acid, fatty acids, such as coco fatty acid and tallow fatty acid, salicylic acid, lactic acid, gluconic acid, citric acid, benzoic acid and ethylenediaminetetraacetic acid; and to anions derived from other types of acids, such as methanesulfonic acid, p-toluenesulfonic acid, boric acid and acid clay.

The compositions of the invention can be prepared in the manner known to the skilled artisan, including but not limited to in-can and tank mix and application of the final formulation may be pre- or post-emergence. Post-emergence application results in particular advantages.

Auxin herbicides especially 2,4-D and dicamba are well known in the art as an effective herbicide for the control various weeds. This class of herbicides has growth promoting effects in cell cultures, specific tissue systems, and intact plants. They have been separated into two groups, one with an oxygen bridge between an aromatic substituent and a carboxylic acid, the other with a carboxyl group directly attached to the aromatic ring. All of these molecules have the free carboxyl group that is required for auxin transport and activity, but the variability of the distance to and the substituents at the aromatic ring system is quite large.

Auxin herbicides are used mainly in grasses (cereal grain crops), turf, coniferous trees (tree nurseries), and certain legumes that are generally quite resistant. They also have utility in pastures, waterways and, in combination with other herbicides, in industrial areas for total vegetation control. Natural dicotyledonous plants including woody plants, are mostly very sensitive and respond to the application of including woody plants, are mostly very sensitive and respond to the application of auxin herbicides by errant growth, necrosis, desiccation, and eventual die-back.

Use

The composition of the present invention is useful as a tank side additive or as a component in a herbicide formulation. In addition the compositions of the present invention are useful as drifting control for other pesticides, such as, fungicides, insecticides, plant growth regulators, acaricides and the like. The pesticide formulations may be wet, dry, slurries or other formulations as are known in the art.

The surfactants can be added directly to a spray tank along with an acid functional pesticide, or as part of a pesticide formulation. When used as a tankside additive, an effective amount of the drift control agent comprising at least one cationic surfactant is generally represented by weight concentrations of from 0.001% to 5.0%, in another embodiment from 0.01% to 1.0%. Likewise, when the surfactants are used in a pesticide formulation (in-can), they are present at weight concentrations that will deliver from about 0.001% to 5.0% to the final use dilution, in another embodiment from about 0.01% to 1.0%, of the final use dilution.

In another embodiment, the cationic surfactant(s) in the final viscoelastic system comprises about 0.01% to about 1.0% by weight of the total viscoelastic drift control pesticidal formulation, the balance being the pesticide, any auxiliary ingredients, and the aqueous medium.

Further Auxiliaries

Suitable auxiliaries are chosen in the customary manner by the skilled artisan in order to meet the performance objectives of the composition. For example, further auxiliaries include, but are not limited to solvents or diluents; emulsifiers, delayed-release agents, pH buffers, antifoams, and the like.

Besides water, the compositions may comprise further solvents of soluble components or diluents of insoluble components of the composition. Examples which are useful in principle are mineral oils, synthetic oils, vegetable oils and animal oils, and low-molecular-weight hydrophilic solvents such as alcohols, ethers, ketones and the like. Those which must therefore be mentioned are, firstly, aprotic or apolar solvents or diluents, such as mineral oil fractions of medium to high boiling point, for example kerosene and diesel oil, furthermore coal tar oils, hydrocarbons, paraffin oils, for example $C_8$- to C30 hydrocarbons of the n- or isoalkane series or mixtures of these, optionally hydrogenated or partially hydrogenated aromatics or alkylaromatics from the benzene or naphthalene series, for example aromatic or cycloaliphatic C7- to C18-hydrocarbon compounds, aliphatic or aromatic carboxylic acid esters or dicarboxylic acid esters, or fats or oils of vegetable or animal origin, such as mono-, di- and triglycerides, in pure form or in the form of a mixture, for example in the form of oily extracts of natural materials, for example olive oil, soya oil, sunflower oil, castor oil, sesame seed oil, corn oil, groundnut oil, rapeseed oil, linseed oil, almond oil, castor oil, safflower oil, and their raffinates, for example hydrogenated or partially hydrogenated products thereof and/or their esters, in particular the methyl and ethyl esters.

Examples of $C_8$- to C30-hydrocarbons of the n- or isoalkane series are n- and isooctane, -decane, -hexadecane, -octadecane, -eicosane, and preferably hydrocarbon mixtures such as liquid paraffin (technical-grade liquid paraffin may comprise up to approximately 5% aromatics) and a C18-C24 mixture which is commercially available from Texaco under the name Spraytex oil.

The aromatic or cycloaliphatic $C_7$ to $C_{18}$ hydrocarbon compounds include, in particular, aromatic or cycloaliphatic solvents from the series of the alkylaromatics. These compounds may be unhydrogenated, partially hydrogenated or fully hydrogenated. Such solvents include, in particular, mono-, di- or trialkylbenzenes, mono-, di- or trialkyl-substituted tetralins and/or mono-, di-, tri- or tetraalkyl-substituted naphthalenes (alkyl is preferably $C_1$-$C_6$-alkyl). Examples of such solvents are toluene, o-, m-, p-xylene, ethylbenzene, isopropylbenzene, tert-butylbenzene and mixtures, such as the Exxon products sold under the names Shellsol and Solvesso, for example Solvesso 100, 150 and 200.

Examples of suitable monocarboxylic esters are oleic esters, in particular methyl oleate and ethyl oleate, lauric esters, in particular 2-ethylhexyl laurate, octyl laurate and isopropyl laurate, isopropyl myristate, palmitic esters, in particular 2-ethylhexyl palmitate and isopropyl palmitate, stearic esters, in particular n-butyl stearate and 2-ethylhexyl 2-ethylhexanoate.

Examples of suitable dicarboxylic esters are adipic esters, in particular dimethyl adipate, di-n-butyl adipate, di-n-octyl adipate, di-iso-octyl adipate, also referred to as bis(2-ethylhexyl) adipate, di-n-nonyl adipate, diisononyl adipate and ditridecyl adipate; succinic esters, in particular di-n-octyl succinate and diisooctyl succinate, and di(isononyl)cyclohexane 1,2-dicarboxylate.

Generally, the above-described aprotic solvents or diluents amount to less than 80% by weight, preferably less than 50% by weight and in particular less than 30% by weight of the total weight of the composition.

Some of these aprotic solvents or diluents may also have adjuvant properties, that is to say in particular synergistic properties. This applies in particular to said mono- and dicarboxylic esters. From this point of view, such adjuvants, perhaps in the form of a part of a further formulation (stand-alone product), may also be mixed with the alcohol alkoxylates according to the invention or with compositions comprising them at an expedient point in time, as a rule shortly prior to application.

Other solvents or diluents that can be employed include protic or polar solvents or diluents, for example $C_2$-$C_8$-monoalcohols such as ethanol, propanol, isopropanol, butanol, isobutanol, tert-butanol, cyclohexanol and 2-ethylhexanol, C3-Cs-ketones such as diethyl ketone, t-butyl methyl ketone and cyclohexanone, and aprotic mines such as N-methyl- and N-octylpyrrolidone.

Generally, the above-described protic or polar solvents or diluents amount to less than 80% by weight, preferably less than 50% by weight and in particular less than 30% by weight of the total weight of the composition.

Sedimentation inhibitors may also be used, in particular for suspension concentrates. Their main purpose is rheological stabilization. Products which must be mentioned in this context are, in particular, mineral products, for example bentonites, talcites and hectorites.

Other additives include mineral salt solutions which are employed for alleviating nutritional and trace element deficiencies, nonphytotoxic oils and oil concentrates, anti-drift reagents, antifoams, in particular the silicone type products, for example Silicon SL, which is sold by Wacker, and the like. The formulations may be present in the form of an emulsifiable concentrate (EC), a suspoemulsion (SE), an oil-in-water emulsion (O/W), a water-in-oil emulsion (W/O), an aqueous suspension concentrate, an oil suspension concentrate (SC), a microemulsion (ME) and the like.

The invention will now be illustrated by the following non-limiting examples.

EXAMPLE 1

Various surfactants were added into 2,4-D solutions at different concentrations. Then the viscosity of the mixture was measured with Brookfield Viscometer. The results show that certain surfactants were more effective to increase the viscosity of the system.

TABLE 1

The effect of tallowalkyl trimethyl ammonium chlorides and electrolyte (2,4-D) concentrations on the viscosity (cPs) of the system (measured with spindle LV#2 at 100 RPM)

| 2.4-D DMA ai % | 1% | 0.50% | 0.25% | 0.13% | 0 |
|---|---|---|---|---|---|
| 0 | 3.3 | 3.3 | 4.2 | 3.9 | 3.3 |
| 0.125 | 3.3 | 3.9 | 10.8 | 4 | 3.3 |
| 0.25 | 4.8 | 25.2 | 9.3 | 4.2 | 3.6 |
| 0.5 | 55.8 | 19.8 | 7.5 | 3.9 | 3.3 |
| 0.75 | 31.8 | 10.8 | 5.7 | 3.6 | 3.6 |
| 1 | 7.8 | 5.1 | 4.2 | 3.6 | 3.3 |
| 1.25 | 4.2 | 3.9 | 3.9 | 3.6 | 3.6 |
| 1.5 | 3.6 | 3.6 | 3.6 | 3.6 | 3.9 |
| 2 | 3.6 | 3.6 | 3.6 | 3.6 | 3.9 |

TABLE 2

The effect of different surfactants on the viscosity (cPs) of the 2,4-D amine salt used as electrolyte system (measured with spindle LV#2 at 100 RPM)

| 2.4-D DMA ai % | 0 | 0.125 | 0.25 | 0.5 | 0.75 | 1 | 1.25 | 1.5 | 2 |
|---|---|---|---|---|---|---|---|---|---|
| 0.5% Cocoalkyltrimethyl ammonium chloride | 3.3 | 3.3 | 3.3 | 4.2 | 3.9 | 3.6 | 3.6 | 3.6 | 3.9 |
| 0.5% Ethoxylated (2) tallowalkyamines | 3.3 | 15 | 21.3 | 5.4 | 4.5 | 3.9 | 3.9 | 7.8 | 4.2 |
| 0.125% Ethoxylated (2) tallowalkyamines | 3 | 3 | 3.3 | 3.3 | 3.3 | 3.3 | 3.6 | 3.3 | 3.5 |
| 0.5% Tris(2-hydroxyethyl)tallowalkyl ammonium acetate | 3.9 | 3.6 | 56.4 | 30.6 | 21.9 | 8.4 | 3.9 | 3.9 | 3.9 |
| 1% Pentamethyltallowalkyl-1,3-propane diammonium dichloride | 3.6 | 3.6 | 3.9 | 3.6 | 3.6 | 3.6 | 3.6 | 3.9 | 3.9 |
| 0.5% Cocoalkylmethylbis(2-hydroxyethyl) ammonium chloride | 3.3 | 3 | 3 | 3.3 | 3 | 3 | 3 | 3 | 3.6 |

EXAMPLE 2

Tub spray method in the lab was used to establish that the 2,4-D amine drift can be reduced by increasing the viscosity of the system. 1 gallon of aqueous solution containing 1% 2,4-D amine (active ingredient) and 0.25% tallowalkyl trimethyl ammonium chlorides (active ingredient) was sprayed at 20 psi with TJ nozzle 8002. Water sensitive paper was placed in front of the spray tub. The paper was moved 30 seconds after the spraying began. The results in the picture showed that indeed viscosity plays an important role in drift control. The drift of aqueous system was significantly reduced in the selected system with higher viscosity compared with herbicide alone (see FIG. 2).

EXAMPLE 3

In this example, a beaker with 100 g of 0.5% a.i. 2,4-D DMA solution containing a stir bar was placed on a magnetic stirrer. The power of the stirrer was adjusted to form a deep vortex in the beaker (the power of the stirrer was kept same for all the testing). Then the surfactants tested were added into the beaker and the amount of surfactant needed to make the "Vortex" disappear was recorded.

TABLE 3

The examples of the surfactants forming the VES system in 2,4-D DMA solution

| List # | Tested Chemical | "Vortex" disappear or Not | Surfactant added |
|---|---|---|---|
| 1 | Ethoxylated (2) tallowalkyamines | Yes | 8.8 |
| 2 | Ethoxylated (5) tallowalkyamines | Yes | 8.175 |
| 3 | Ethoxylated (2) oleylamines | Yes | 9.80 |
| 4 | Fatty alkanolamide | Yes | 10.57 |
| 5 | Tris(2-hydroxyethyl) tallowalkyl ammonium acetates | Yes | 2.90 |
| 6 | N-methyl-N,N-bis(2-hydroxyethyl)erucylammonium chloride | Yes | 3.4 |
| 7 | Tallowalkyltrimethyl ammonium chlorides | Yes | 1.3 |
| 8 | Hexadecylalkyltrimethyl ammonium chlorides | Yes | 1.7 |
| 9 | Amides, tallow, n-[3-(dimethylamino)propyl | Yes | 5.3 |
| 10 | Amides, coco, n-[3-(dimethylamino)propyl | Yes | 8.76 |
| 11 | amides, tallow, n-[3-(dimethylamino)propyl], n-oxides | Yes | 5.3 |
| 12 | amides, oley, n-[3-(dimethylamino)propyl], n-oxides | Yes | 0.3 |
| 13 | N-[3-dimethylaminopropyl)erucamide oxide | Yes | 3.7 |
| 14 | Tallow dimethyl betaine | Yes | 4.9 |
| 15 | TOFA amido propyl betaine | Yes | 9.2 |

I claim

1. A method of reducing spray drift of an aqueous pesticidal formulation comprising at least one pesticide which contains at least one acid functional group, said method comprising
    adding to said formulation at least one drift control agent which comprises a nitrogen-based surfactant, wherein the acid functional group of said pesticide is capable of associating with said surfactant thereby forming a viscoelastic pesticidal system having reduced drift;
wherein the surfactant is present at a weight concentration of 0.5% and the pesticide is present at weight concentrations from 0.25% to 0.75% and the at least one surfactant is represented by general formula (C)

$$R^4 - N^+ \begin{matrix} (CH_2CH_2O)_n\ H \\ \diagdown \\ -Z \\ \diagup \\ (CH_2CH_2O)_m\ H \end{matrix} \quad X^- \tag{C}$$

where $R^4$ is C12 to C30 linear or branched, saturated or unsaturated hydrocarbon chain; n=1-4, m=1-4; Z is $CH_3$, $C_1$-$C_4$ alkyl or hydroxyl alkyl; and $X^-$ is an anion; wherein the pesticide is (2,4-dichlorophenoxy)acetic acid dimethyl amine salt and the surfactant is tris(2-hydroxyethyl)tallowalkyl ammonium acetate.

2. A method of reducing spray drift of an aqueous pesticidal formulation comprising at least one pesticide which contains at least one acid functional group, said method comprising adding to said formulation at least one drift control agent which comprises a nitrogen-based surfactant, wherein the acid functional group of said pesticide is capable of associating with said surfactant thereby forming a viscoelastic pesticidal system having reduced drift; wherein the surfactant is present at a weight concentrations from 0.5% to 0.75% and the pesticide is present at weight concentrations from 0.50% to 1% and the at least one surfactant is represented by general formula (F)

(F)

(F)

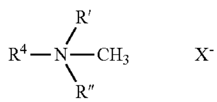

R4 is C12 to C30 to C30 linear or branched, saturated or unsaturated hydrocarbon chain;

R' and R" are C1-C4 linear and branched alkyl group, and $X^-$ is an anion; wherein the pesticide is (2,4-dichlorophenoxy)acetic acid dimethyl amine salt and the surfactant is tris(2-hydroxyethyl)tallowalkyl ammonium acetate.

* * * * *